(12) United States Patent
Yang et al.

(10) Patent No.: US 10,366,491 B2
(45) Date of Patent: Jul. 30, 2019

(54) DEEP IMAGE-TO-IMAGE RECURRENT NETWORK WITH SHAPE BASIS FOR AUTOMATIC VERTEBRA LABELING IN LARGE-SCALE 3D CT VOLUMES

(71) Applicant: Siemens Healthcare GmbH, Erlangen (DE)

(72) Inventors: Dong Yang, Somerset, NJ (US); Tao Xiong, Baltimore, MD (US); Daguang Xu, Princeton, NJ (US); Shaohua Kevin Zhou, Plainsboro, NJ (US); Mingqing Chen, Plainsboro, NJ (US); Zhoubing Xu, Plainsboro, NJ (US); Dorin Comaniciu, Princeton Junction, NJ (US); Jin-hyeong Park, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 64 days.

(21) Appl. No.: 15/886,873

(22) Filed: Feb. 2, 2018

(65) Prior Publication Data
US 2018/0260951 A1    Sep. 13, 2018

Related U.S. Application Data

(60) Provisional application No. 62/468,641, filed on Mar. 8, 2017.

(51) Int. Cl.
*A61B 6/00* (2006.01)
*G06T 7/00* (2017.01)
(Continued)

(52) U.S. Cl.
CPC ........... *G06T 7/0012* (2013.01); *A61B 5/004* (2013.01); *A61B 5/0073* (2013.01);
(Continued)

(58) Field of Classification Search
CPC .................................. G06T 7/00; G06K 9/00
(Continued)

(56) References Cited

U.S. PATENT DOCUMENTS

| 7,903,851 B2 | 3/2011 | Reisman et al. |
| 8,965,083 B2* | 2/2015 | Ben Ayed ............... G06T 7/136 382/128 |

(Continued)

OTHER PUBLICATIONS

Glocker et al., "Automatic Localization and Identification of Vertebrae in Arbitrary Field-of-View CT Scans"; In International Conference on Medical Image Computing and Computer-Assisted Intervention; Springer Berlin Heidelberg; Oct. 2012; 8 pgs.

(Continued)

*Primary Examiner* — Abolfazl Tabatabai

(57) ABSTRACT

A method and apparatus for automated vertebra localization and identification in a 3D computed tomography (CT) volumes is disclosed. Initial vertebra locations in a 3D CT volume of a patient are predicted for a plurality of vertebrae corresponding to a plurality of vertebra labels using a trained deep image-to-image network (DI2IN). The initial vertebra locations for the plurality of vertebrae predicted using the DI2IN are refined using a trained recurrent neural network, resulting in an updated set of vertebra locations for the plurality of vertebrae corresponding to the plurality of vertebrae labels. Final vertebra locations in the 3D CT volume for the plurality of vertebrae corresponding to the plurality of vertebra labels are determined by refining the updated set of vertebra locations using a trained shape-basis deep neural network.

23 Claims, 9 Drawing Sheets

(51) Int. Cl.

| | | |
|---|---|---|
| *G06T 7/11* | (2017.01) | |
| *G06K 9/66* | (2006.01) | |
| *G06K 9/00* | (2006.01) | |
| *A61B 6/03* | (2006.01) | |
| *A61B 5/00* | (2006.01) | |
| *G06N 3/08* | (2006.01) | |
| *G16H 30/40* | (2018.01) | |
| *G06K 9/62* | (2006.01) | |
| *G06N 3/04* | (2006.01) | |
| *G06T 7/73* | (2017.01) | |
| *A61B 1/32* | (2006.01) | |

(52) U.S. Cl.
CPC .......... *A61B 5/4566* (2013.01); *A61B 5/4887* (2013.01); *A61B 5/7267* (2013.01); *A61B 6/032* (2013.01); *A61B 6/505* (2013.01); *A61B 6/5217* (2013.01); *G06K 9/00718* (2013.01); *G06K 9/6267* (2013.01); *G06K 9/66* (2013.01); *G06N 3/0445* (2013.01); *G06N 3/0454* (2013.01); *G06N 3/08* (2013.01); *G06N 3/084* (2013.01); *G06T 7/11* (2017.01); *G06T 7/74* (2017.01); *G16H 30/40* (2018.01); *G06K 9/00201* (2013.01); *G06K 2209/05* (2013.01); *G06T 2207/10081* (2013.01); *G06T 2207/20081* (2013.01); *G06T 2207/20084* (2013.01); *G06T 2207/30012* (2013.01)

(58) Field of Classification Search
USPC ......................................................... 382/131
See application file for complete search history.

(56) References Cited

U.S. PATENT DOCUMENTS

| | | | |
|---|---|---|---|
| 9,401,020 | B1 | 7/2016 | Li et al. |
| 9,406,122 | B2 * | 8/2016 | Hladuvka ................ G06T 7/11 |
| 9,760,807 | B2 | 9/2017 | Zhou et al. |
| 2016/0089074 | A1 | 3/2016 | Wang |

OTHER PUBLICATIONS

Glocker et al., "Vertebrae Localization in Pathological Spine CT Via Dense Classification from Sparse Annotations"; In International Conference on Medical Image Computing and Computer-Assisted Intervention; Springer Berlin Heidelberg; Sep. 2013; 8 pgs.

Chen et al., "Automatic Localization and Identification of Vertebrae in Spine CT Via a Joint Learning Model with Deep Neural Networks"; In International Conference on Medical Image Computing and Computer-Assisted Intervention; Springer International Publishing; Oct. 2015; pp. 515-522.

Suzani et al., Fast Automatic Vertebrae Detection and Localization in Pathological CT Scans—A Deep Learning Appoach; In International Conference on Medical Image Computing and Computer-Assisted Intervention; Springer International Publishing; Oct. 2015; pp. 678-686.

Payer et al., "Regressing Heatmaps for Multiple Landmark Localization Using CNNs"; In International Conference on Medical Image Computing and Computer-Assisted Intervention; Springer International Publishing; Oct. 2016; 9 pgs.

Badrinarayanan et al., "SegNet: A Deep Convolutional Encoder-Decoder Architecture for Image Segmentation"; Oct. 10, 2016; 14 pgs.

Ronneberger et al., "U-Net: Convolutional Networks for Biomedical Image Segmentation"; In International Conference on Medical Image Computing and Computer-Assisted Intervention; Springer International Publishing; May 18, 2015; pp. 234-241.

Xie et al., "Holistically-Nested Edge Detection"; In Proceedings of the IEEE International Conference on Computer Vision; 10 pgs.

Merkow et al., "Dense Volume-to-Volume Vascular Boundary Detection"; Unversity of California, San Diego; Stanford University; 8 pgs.

Dou et al., "3D Deeply Supervised Network for Automatic Liver Segmentation from CT Volumes"; MICCAI; Springer International Publishing; Jul. 3, 2016; 8 pgs.

Yu et al, "Deep Deformation Network for Object Landmark Localization"; In European Conference on Computer Vision; Springer International Publishing; Oct. 2016; 17 pgs.

* cited by examiner

FIG. 7

| Region | Method | Set 1 | | | Set 2 | | |
|---|---|---|---|---|---|---|---|
| | | Mean | Std | Id.Rates | Mean | Std | Id.Rates |
| All | Glocker et al [2] | 12.4 | 11.2 | 70% | 13.2 | 17.8 | 74% |
| | Suzani et al | 18.2 | 11.4 | - | - | - | - |
| | Chen et al | - | - | - | 8.8 | 13.0 | 84% |
| | DI2IN | 17.0 | 47.3 | 74% | 13.6 | 37.5 | 76% |
| | DI2IN+ConvLSTM | 15.2 | 37.7 | 76% | 10.4 | 13.5 | 78% |
| | DI2IN+ConvLSTM+Shape | 10.6 | 8.7 | 78% | 8.7 | 8.5 | 85% |
| | DI2IN+1000 | 10.6 | 21.5 | 80% | 7.1 | 11.8 | 87% |
| | DI2IN+ConvLSTM+1000 | 10.0 | 19.0 | 81% | 7.1 | 8.3 | 88% |
| | DI2IN+ConvLSTM+Shape+1000 | 9.0 | 8.8 | 82% | 6.9 | 7.6 | 89% |
| Cervical | Glocker et al [2] | 7.0 | 4.7 | 80% | 6.8 | 10.0 | 89% |
| | Suzani et al | 17.1 | 8.7 | - | - | - | - |
| | Chen et al | - | - | - | 5.1 | 8.2 | 92% |
| | DI2IN+ConvLSTM+Shape | 7.5 | 5.5 | 87% | 5.8 | 5.0 | 91% |
| | DI2IN+ConvLSTM+Shape+1000 | 6.4 | 5.2 | 89% | 5.2 | 4.8 | 93% |
| Thoracic | Glocker et al [2] | 13.8 | 11.8 | 62% | 17.4 | 22.3 | 62% |
| | Suzani et al | 17.2 | 11.8 | - | - | - | - |
| | Chen et al | - | - | - | 11.4 | 16.5 | 76% |
| | DI2IN+ConvLSTM+Shape | 11.4 | 9.0 | 73% | 7.8 | 9.1 | 79% |
| | DI2IN+ConvLSM+Shape+1000 | 9.7 | 9.1 | 76% | 7.4 | 7.8 | 85% |
| Lumbar | Glocker et al [2] | 14.3 | 12.3 | 75% | 13.0 | 12.5 | 80% |
| | Suzani et al | 20.3 | 12.2 | - | - | - | - |
| | Chen et al | - | - | - | 8.4 | 8.6 | 88% |
| | DI2IN+ConvLSTM+Shape | 12.4 | 9.9 | 78% | 12.1 | 11.8 | 81% |
| | DI2IN+ConvLSTM+Shape+1000 | 11.2 | 12.0 | 83% | 8.1 | 9.4 | 88% |

DEEP IMAGE-TO-IMAGE RECURRENT NETWORK WITH SHAPE BASIS FOR AUTOMATIC VERTEBRA LABELING IN LARGE-SCALE 3D CT VOLUMES

This application claims the benefit of U.S. Provisional Application No. 62/468,641, filed Mar. 8, 2017, the disclosure of which is herein incorporated by reference.

BACKGROUND OF THE INVENTION

The present invention relates to automated localization and identification of vertebrae in medical images, and more particularly, to automated deep-learning based localization and identification of vertebrae in 3D computed tomography (CT) volumes.

Accurate and automatic localization and identification of human vertebrae in 3D spinal imaging is important for clinical tasks such as pathological diagnosis, surgical planning, and post-operative assessment of pathologies. Specific applications, such as vertebrae segmentation, fracture detection, tumor detection and localization, registration, and statistical shape analysis can benefit from efficient and precise automated vertebrae detection and labeling algorithms. However, such automated vertebrae detection and labeling algorithms must address various challenges including pathological cases, image artifacts, and limited field-of-view (FOV). Various approaches for automated vertebrae detection have been developed to address these challenges. However, a method for automatic vertebrae localization and identification that can provide improvements in accuracy and efficiency over existing approaches is desirable.

BRIEF SUMMARY OF THE INVENTION

The present invention provides a method and system for automated computer-based detection and labeling of vertebrae in 3D computed tomography (CT) volumes. Embodiments of the present invention utilize a deep image-to-image network (DI2IN) to detect initial vertebra locations in a 3D CT volume of a patient. Embodiments of the present model probability maps utilize a recurrent neural network (RNN) to model the spatial relationship of vertebra response from the DI2IN and refine the detected vertebra locations. Embodiments of the present invention utilize a shape basis network with a learned shape basis to further refine and regularize the detected vertebra locations.

In one embodiment of the present invention, initial vertebra locations in a 3D CT volume of a patient are predicted for a plurality of vertebrae corresponding to a plurality of vertebra labels using a trained deep image-to-image network (DI2IN). The initial vertebra locations for the plurality of vertebrae predicted using the DI2IN are refined using a trained recurrent neural network, resulting in an updated set of vertebra locations for the plurality of vertebrae corresponding to the plurality of vertebra labels. Final vertebra locations in the 3D CT volume for the plurality of vertebrae corresponding to the plurality of vertebra labels are determined by refining the updated set of vertebra locations using a trained shape-basis deep neural network.

These and other advantages of the invention will be apparent to those of ordinary skill in the art by reference to the following detailed description and the accompanying drawings.

BRIEF DESCRIPTION OF THE DRAWINGS

FIG. 7 illustrates a comparison of localization errors and identification rates among different methods;

DETAILED DESCRIPTION

Figure 1:
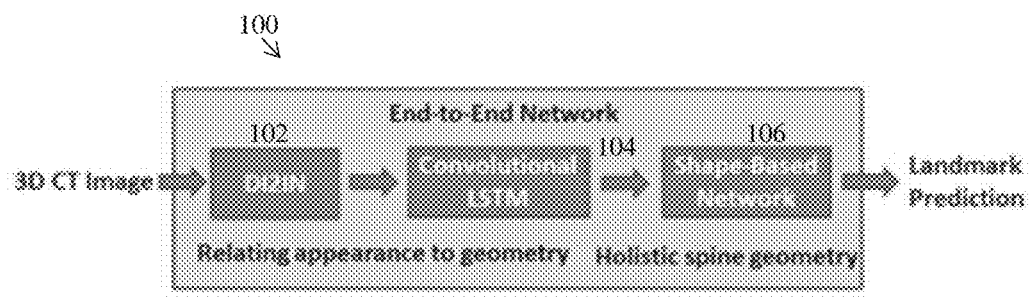
FIG. 1. Illustrates a framework for automated detection and labeling of vertebrae in 3D computed tomography (CT) volumes according to an embodiment of the present invention.

The present invention relates to a method and system for automated computer-based detection and labeling of vertebrae in 3D computed tomography (CT) volumes. Embodiments of the present invention are described herein to give a visual understanding of the method for automated detection and labeling of vertebrae. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Various approaches have been proposed to address the challenges in automatic vertebrae detection. Glocker et al., "Automatic Localization and Identification of Vertebrae in Arbitrary Field-of-View CT Scans", *International Conference on Medical Image Computing and Computer-Assisted Intervention*, October 2012, pp. 590-598 (hereinafter "Glocker et al. [1]"), presented a two-stage approach for localization and identification of vertebrae in CT, which has achieved an identification rate of 81%. This approach uses regression forests and a generative model for prediction and requires handcrafted feature vectors in pre-processing. Glocker et al., "Vertebrae Localization in Pathological Spine CT via Dense Classification from Sparse Annotations", *International Conference on Medical Image Computing and Computer-Assisted Intervention*, September 2013, pp. 262-270 (hereinafter "Glocker et al. [2]"), further extended the vertebrae localization to handle pathological spine CT. This supervised classification forests based approach achieves an identification rate of 70% on a pathological database. Recently, Chen et al., "Automatic Localization and Identification of Vertebrae in Spine CT via a Joint Learning Model with Deep Neural Networks", *International Conference on Medical Image Computing and Computer-Assisted Intervention*, October 2015, pp. 512-522 (hereinafter "Chen et al."), proposed a joint learning model with deep neural networks (J-CNN) designed to effectively identify the type of vertebra. This approach improved the identification rate (85%) by a large margin. This approach trains a random forest classifier to coarsely detect vertebral centroids instead of directly performing the neural network on whole CT volumes. Suzani et al., "Fast Automatic Vertebrae Detection and Localization in Pathological CT Scans—A Deep Learning Approach", *International Conference on Medical Image Computing and Computer-Assisted Intervention*, October 2015, pp. 678-686 (hereinafter "Suzani et al.")also presented a deep neural network for fast vertebrae detection. This approach first extracts intensity-based features, then uses a deep neural network to localize the vertebrae. Although this approach has achieved a high detection rate, it suffers from a large mean error compared to other approaches.

Embodiments of the present invention utilize deep neural networks for automatic localization (detection) and identification (labeling) of vertebrae in 3D CT volumes, and provide improvements in both accuracy and efficiency as compared with existing approaches. FIG. 1. Illustrates a framework for automated detection and labeling of vertebrae in 3D CT volumes according to an embodiment of the present invention. As shown in FIG. 1, an end-to-end network 100 includes the following components for generating landmark predictions corresponding to labeled vertebrae from a 3D CT image (volume): a deep image-to-image network 102, a convolutional long short-term memory (LSTM) network 104, and a shape-based network 106. In a first stage, the DI2IN 102 is used for voxel-wise regression. Instead of extracting handcrafted features or adopting coarse classifiers, the DI2IN 102 directly performs on the 3D CT volume and outputs multi-channel probability maps associated with different vertebrae centers. The high responses in the probability maps intuitively indicate the location and label of the vertebrae. The training of the DI2IN 102 is formulated as a multi-channel voxel-wise regression. Since the DI2IN 102 is implemented in a fully convolutional way, it is significantly more efficient is computational time as compared to sliding window approaches. In a second stage, a recurrent neural network (RNN) is used to model the spatial relationship of vertebra responses from the DI2IN 102. The vertebrae can be interpreted in a chain structure from head to hip according to their related positions. The sequential order of the chain-structured model enables the vertebra responses to communicate with each using a recurrent model, such as an RNN. According to an advantageous embodiment, a convolutional LSTM 104 is used as the RNN to capture the spatial correlation between vertebra predictions. The convolutional LSTM 104 studies pair-wise relation of vertebra responses and regularizes the output of the DI2IN 102. In a third stage, the shape-basis network 106, which takes advantage of the holistic structure of the spine, is utilized to further refine the coordinates of the vertebrae. Instead of learning a quadratic regression model to file the spinal shape, the coordinates of spines in training samples are used to construct a shape-based dictionary and formulate the training process as a regression problem. The shape-basis neural network 106 extracts coordinates from the previous stage (104) as input and generates the coefficients associated with the dictionary, which indicates the linear combination of atoms from the shape-based dictionary. By embedding the shape regularity in the training of a neural network, ambiguous coordinates are removed and the representation is optimized, which further improves the localization and identification performance. Compared with existing methods which apply classic refinement methods as a post-processing step, embodiments of the present invention introduce an end-to-end training network that performs the refinement step. The whole pipeline of FIG. 1 is conducted in an end-to-end manner.

Figure 2:
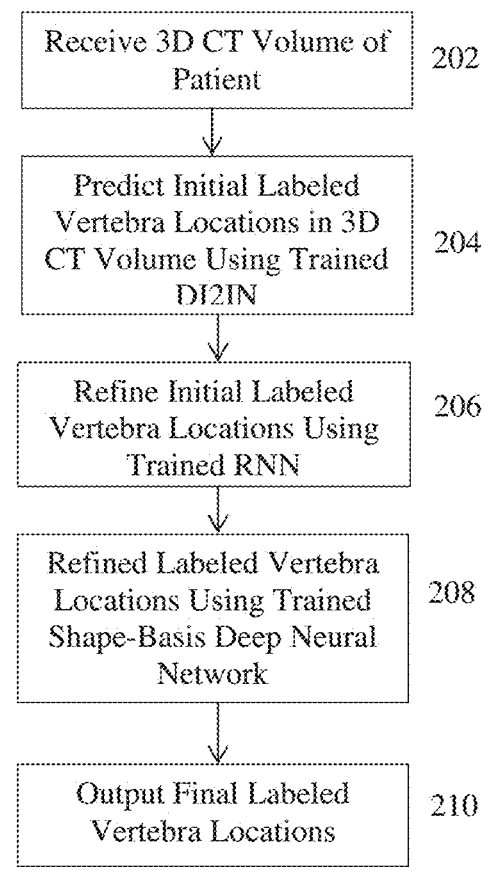
FIG. 2 illustrates a method for automated detection and labeling of vertebrae in a 3D CT volume according to an embodiment of the present invention.

FIG. 2 illustrates a method for automated detection and labeling of vertebrae in a 3D CT volume according to an embodiment of the present invention. The method of FIG. 2 provides additional details for the pipeline illustrated in FIG. 1. Referring to FIG. 2, at step 202, a 3D CT volume of a patient is received. The 3D CT volume includes a spine region of the patient. For example, the 3D CT volume may a spine CT volume or a whole-body CT volume. The 3D CT volume may be received directly from an image acquisition device, such as a CT scanner, or may be received by loading a previously acquired CT volume from a memory or storage of a computer system or as an electronic transmission from a remote computer system.

At step 204, initial labeled vertebra locations in the 3D CT volume are predicted using a trained deep image-to-image network (DI2IN). The trained DI2IN performs voxel-wise regression on the 3D CT volume and predicts initial vertebra locations for a set of labeled vertebrae by generating a respective probability map corresponding to each of a plurality of vertebra labels. In an advantageous implementation, the DI2IN generates 26 probability maps corresponding to seven cervical vertebrae (C1-C7), twelve thoracic vertebrae (T1-T12), five lumbar vertebrae (L1-L5) and two sacral vertebrae (S1-S2).

According to an advantageous embodiment, a convolutional encoder-decoder network architecture is used to implement the DI2IN. Compared to a sliding window approach, the DI2IN is implemented using voxel-wise fully convolutional end-to-end learning. The DI2IN performs the network on the input 3D CT volume directly. In particular, the DI2IN takes the 3D CT volume as input and generates the multi-channel probability maps corresponding to the plurality of vertebra labels (C1-S2) simultaneously. Each of the multi-channel probability maps is a 3D image (volume) of the same size as the input 3D CT volume that provides probability for each voxel that the voxel is the location of the vertebra of the label associated with that probability map. The DI2IN is trained based on training image and corresponding ground truth probability maps generated from the training images. The ground truth probability maps (for each vertebra label) are generated based on annotated ground truth vertebra locations in the training images by a Gaussian distribution $I_{gt}=$ $$\frac{1}{\sigma 2\sqrt{2\pi}} e^{-\|x-\mu\|^2/2\sigma^2},$$

where $x \in \mathbb{R}^3$ denotes the voxel coordinates and $\mu$ denotes the ground truth vertebra location. The standard deviation $\sigma$ is preset to control the scale of the Gaussian distribution. Each channel's predicted probability map $I_{prediction}$ is associated with the centroid location and type (label) of vertebra. The loss function is defined as $\|I_{prediction}-I_{gt}\|^2$ for each voxel. Accordingly, the whole learning problem is formulated as a multi-channel voxel-wise regression. Instead of using classification formulation for detection, regression is very helpful for determining predicted coordinates and it relieves the issue of imbalanced training samples, which is very common in semantic segmentation.

Figure 3:
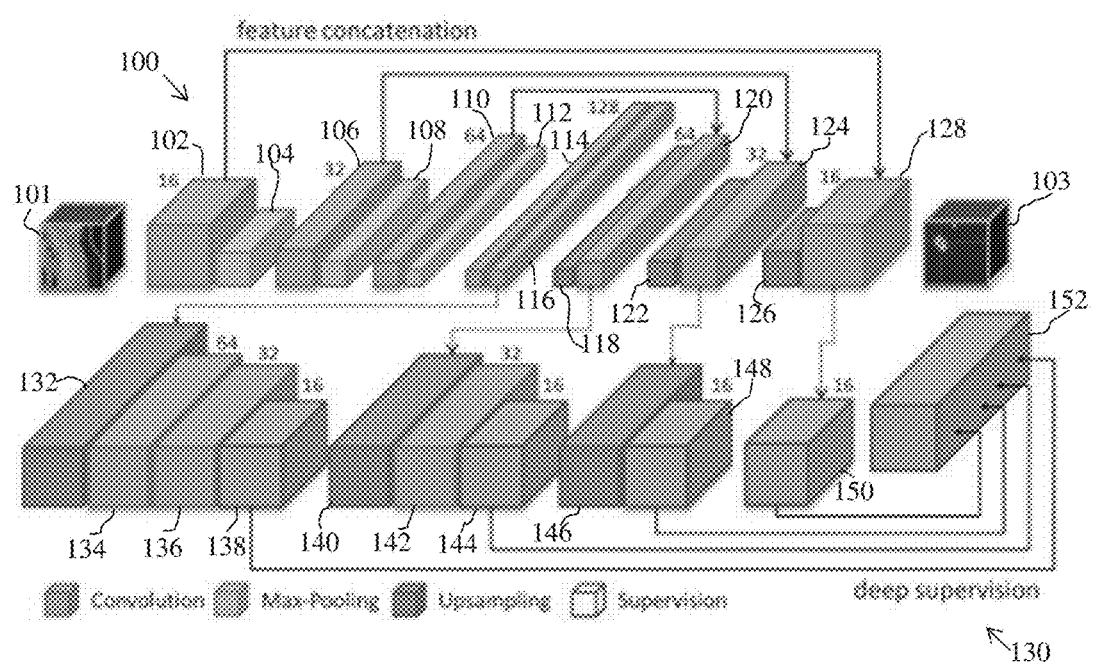
FIG. 3 illustrates a network architecture for a deep image-to-image network (DI2IN) according to an embodiment of the present invention.

FIG. 3 illustrates a network architecture for the deep image-to-image network (DI2IN) according to an embodiment of the present invention. As shown in FIG. 3, the front part of the DI2IN is a convolutional encoder-decoder network 100 with feature concatenation and the backed is a multi-level deep supervision network 130. Layers 102, 106, 110, 114, 116, 120, 124, 134, 136, 138, 142, 144, 148, 150, and 152 are convolutional layers. Numbers next to convolutional layers 102, 106, 110, 114, 116, 120, 124, 134, 136, 138, 142, 144, 148, and 150 are channel numbers. Layers 104, 108, and 112 are max-pooling layers. Layers 118, 122, 126, 132, 140, and 146 are up-sampling layers. Layers 138, 144, 148, and 152 perform deep supervision. The convolutional encoder-decoder network 100 includes an encoder (layers 102-114) and a decoder (layers 116-128). The encoder (layers 102-114) includes convolutional, rectified linear unit (ReLU), and max-pooling layers, while the decoder (layers 116-128) includes convolutional, ReLU, and up-sampling layers. The max-pooling layers 104, 108, and 112 are advantageous in that they increase the receptive field and extract large contextual information. The up-sampling layers 118, 122, and 126 utilize bilinear interpolation to enlarge and densify the activation, which enables end-to-end voxel-wise training without losing resolution details. In an advantageous implementation, the convolutional filter size is 1×1×1 in the output layer and 3×3×3 in other layers. The max-pooling filter size is 2×2×2 for down-sampling by half in each dimension. The stride is set as 1 in order to maintain the same size in each channel. Additionally, the DI2IN of FIG. 3 incorporates feature concatenation and deep supervision. In the feature concatenation, a bridge is built directly from the encoder layer to the corresponding decoder layer and feature information from the encoder layer is passed directly to the corresponding decoder layer via the bridge and concatenated with the decoder layer. As a result, the DI2IN benefits from local and global contextual information.

According to an advantageous embodiment, the DI2IN utilizes the multi-level deep supervision network 130, which incorporates a more complex deep supervision approach than typical deep learning methods, to improve the performance of the DI2IN. In the deep supervision network 130, several branches (e.g., layers 132-138, layers 140-144, and layers 146-148) are diverged from the middle layers of the decoder network. Extra 26-channel convolution layers are implicitly used in the deep supervision, such that the output layer of each branch outputs a respective output feature map for each of the 26 vertebra labels. With the appropriate up-sampling and convolutional operations as shown in FIG. 3, the output size of the output layer of each branch matches the size of the 26-channel ground truth. Accordingly, each of the branches of the deep supervision network 130 generates a respective probability map (for each channel) based on the feature map output by the respective decoder layer. Layer 150 generates a predicted final probability map based on the feature map output by the final decoder layer. In training of the DI2IN, in order to take advantage of the multi-layer deep supervision, the total loss function $l_{total}$ of the DI2IN is defined as the combination of loss $l_i$ for all output branches and loss $l_{final}$ of the final output as follows:

$$l_{total} = \sum_i l_i + l_{final}.$$

As described above, the loss $l_i$ for each output branches and the loss $l_{final}$ for the final output can be calculated as $|I_{prediction} - I_{gt}|^2$. During training, gradient descent back-propagation is used to learn weights for the layers of the DI2IN to minimize the total loss function $l_{total}$.

Returning to FIG. 2, at step 206, the initial labeled vertebra locations are refined using a trained recurrent neural network (RNN). In an advantageous embodiment, the trained RNN is a multi-layer convolutional LSTM. Given the 3D CT image I, the DI2IN generates a probability map $P(v_i|I)$ for the centroid of each vertebra i with high confidence. The vertebrae are localized at the peak positions $v_i$ of the probability maps. However, these probability maps will likely not be perfect. Some of the probability maps for some vertebra labels may not have a response or may have a very low response at the ground truth locations because of similar image appearances if several vertebrae (e.g., T1~T12). In order to handle the problem of missing or low response at the ground truth location for a vertebra center, the RNN enhances/refines the probability maps output by the DI2IN by incorporating knowledge of spinal structure from the entire set of probability maps.

RNN has been developed and used in applications such as natural language processing or video analysis. RNN is capable of handling arbitrary sequences of input and performs the same processing on every element of the sequence with memory of the previous computation. According to an advantageous embodiment, the spatial relation of vertebrae forms a chain structure from top (C1) to bottom (S2). Each element of the chain is the response map (probability map) of the respective vertebra center. The RNN treats the chain of probability maps as a sequence and enables information from the different vertebra probability maps to be shared in order to refine the probability maps. In an advantageous embodiment, a convolutional LSTM is uses as the RNN model to refine the 3D probability maps of the vertebrae generated by the DI2IN.

Figure 4:
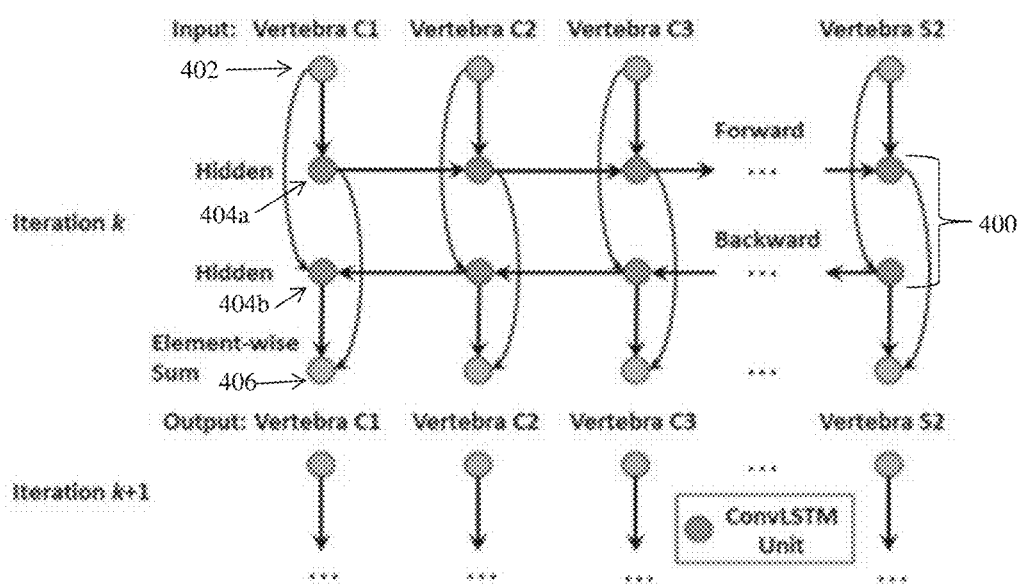
FIG. 4 illustrates updating vertebra probability maps using a multi-layer convolutional long short-term memory (LSTM) according to an embodiment of the present invention.

FIG. 4 illustrates updating the vertebra probability maps using a multi-layer convolutional LSTM according to an embodiment of the present invention. As shown in FIG. 4, a multi-layer convolutional LSTM 404 sequentially inputs the vertebra probability map 402 for each vertebra and outputs a respective updated probability map 404 for each vertebra. Because the z direction (vertical with respect to the patient) is the most informative dimension, the x, y dimensions are set to 1 for all convolutional kernels. During inference, information is passed forward (from top to bottom) and backward (from bottom to top) to regularize the output of the DI2IN. In particular, the multi-layer convolutional LSTM 404 includes a forward convolutional LSTM layer 404a and a backward convolutional LSTM layer 404b, and the probability maps 402 are sequentially input to the forward convolutional LSTM layer 404a in order from the C1 vertebra to the S2 vertebra and sequentially input to the backward convolutional LSTM layer 404b in reverse order from the S2 vertebra to the C1 vertebra. For a given input probability map for a particular vertebra, a first updated probability map is generated by the forward convolutional LSTM layer 404a and a second updated probability map is generated by the backward convolutional LSTM layer 404b. The first and second updated probability maps are combined using an element-wise sum, and the resulting updated probability map 406 is output by the convolutional LSTM 404. The refinement by the convolutional LSTM 404 can be repeated for k iterations (e.g., k=2), with output probability maps from one iteration used as the input for the next iteration. The convolution LSTM unit in the forward convolutional LSTM layer 404a and backward convolutional LSTM layer 404b includes a plurality of hidden layers. All input-to-hidden and hidden-to-hidden operations are convolution. Therefore, the response distributions (probability maps) can be adjusted with necessary displacement or enhanced based on the neighboring responses (i.e., the probability maps for neighboring vertebrae.

The convolutional LSTM (in both forward and backward directions) treats the spatial sequence of vertebra probability maps as if it was a time sequence. Accordingly, at a given "time step" the LSTM unit inputs a given vertebra probability map and information from the previous time step and outputs an updated vertebra probability map. The following equations describe how the LSTM unit is updated at each time:

$$i_t = \sigma(G_{xi}(X_t) + G_{hi}(H_{t-1}) + W_{ci} \odot C_{t-1} + b_i)$$

$$f_t = \sigma(G_{xf}(X_t) + G_{hf}(H_{t-1}) + W_{cf} \odot C_{t-1} + b_f)$$

$$C_t = f_t \odot C_{t-1} + i_t \odot \tanh(G_{xc}(X_t) + G_{hc}(H_{t-1}) + b_c)$$

$$o_t = \sigma(G_{xo}(X_t) + G_{ho}(H_{t-1}) + W_{co} \odot C_t + b_o)$$

$$H_t = o_t \odot \tanh(C_t).$$

$X_1, X_2, \ldots, X_T$ are input states for the respective vertebrae, $C_1, C_2, \ldots, C_T$ are cell states, and $H_1, H_2, \ldots, H_T$. Accordingly, $X_t$, $C_t$, and $H_t$ denote the input probability map, the cell state, and the hidden state for a current vertebra (i.e., at a current time step). $i_t$, $f_t$, and $o_t$ are gate functions of the input gate, forget gate, and output gate, respectively, of the convolutional LSTM. Accordingly to an advantageous implementation, several sub-networks G are used to update $X_t$ and $H_t$ which differs from traditional convolutional LSTMs, which only use a single kernel. Each G includes three convolutional layers with 1×1×9 kernels, and the filter numbers for the three layers are 9, 1, and 1, respectively. These sub-networks are more flexible and have a larger receptive field compared to a network that uses a single kernel. Therefore, these subnetworks are advantageous for capturing the spatial relationship of the vertebrae. During training, weights for G and W, as well as biases b, are learned during training of the LSTM based on training data.

Figure 5:
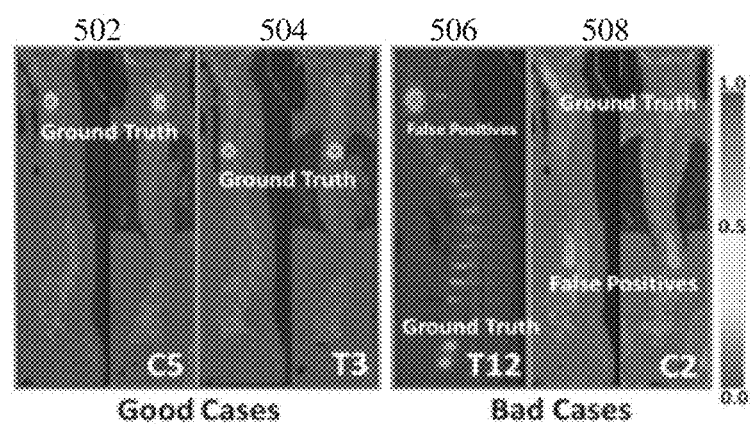
FIG. 5 illustrates exemplary vertebra probability maps generated by the DI2IN and the convolutional LSTM.

Returning to FIG. 1, at step 208, the labeled vertebra locations are further refined using a trained shape-basis deep neural network. In step 206, the convolutional LSTM generates updated probability maps, where the high response in a probability map for a particular vertebra indicates the potential location of the centroid of that vertebra in the 3D CT volume. However, in some cases, due to image artifacts and/or low image resolution, it may be difficult to guarantee that there are no false positive predicted vertebra locations. FIG. 5 illustrates exemplary vertebra probability maps generated by the DI2IN and the convolutional LSTM. Image 502 shows a probability map for the C5 vertebra generated by the DI2IN. Image 504 shows a probability map for the T3 vertebra output by the convolutional LSTM. Images 502 and 504 show examples of "good cases" in which the ground truth is close to the predicted vertebra location in the probability map. Image 506 shows a probability map for the T12 vertebra generated by the DI2IN. Image 508 shows a probability map for the C2 vertebra output by the convolutional LSTM. Images 506 and 508 show examples of "bad cases" in which some false positives with high probability exist in the probability map that are remote from the actual ground truth location of the particular vertebra associated with the probability map. According to an advantageous embodiment, a shape-basis network is used to further refine the detected vertebrae coordinates.

Given a pre-defined shape-based dictionary $D \in \mathbb{R}^{N \times M}$ and coordinate vector $y \in \mathbb{R}^N$ generated from the probability maps by the convolutional LSTM, the shape-basis network takes y as input and outputs a coefficient vector $x \in \mathbb{R}^M$ associated with the dictionary D. The refined coordinate vector $\hat{y}$ is then defined as $\hat{y} = Dx$. In an advantageous implementation, the shape-based dictionary D is learned from a set of annotated training samples. For example, the dictionary $D_z$ associated with the vertical axis is constructed by the z coordinates of the vertebrae centroids in the training samples. N and M indicate the number of vertebrae and the number of atoms in the dictionary, respectively.

In an advantageous implementation, the shape-basis network is a deep neural network having several fully connected layers. Instead of regressing the refined coordinates, the network is trained to regress the coefficients x associated with the shape-based dictionary D. During training, the learning problem is formulated as a regression model and the loss function is defined as:

$$\text{loss} = \sum_i \|Dx_i - y_i\|_2^2 + \lambda \|x_i\|_1.$$

In this loss function, $x_i$ and $y_i$ denote the predicted coefficient vector and the ground truth coordinate vector for the ith training sample. $\lambda$ is the $l_1$ norm coefficient to leverage sparsity and residual. Based on the loss function, the shape-basis neural network is learned to find the best linear combination (of atoms) in the learned dictionary to refine the coordinates over a set of training samples. In particular, weights of the shape-basis neural network are learned to minimize the loss function over the set of training samples, for example using gradient descent back propagation.

The input of the shape-basis network is a coordinate vector including the coordinates for the locations of centroid of each vertebra that is generated from the refined probability maps output by the convolutional LSTM, for example by selecting a voxel location having the highest probability in each of the probability. In an advantageous embodiment, the input coordinate vector for the shape-basis network is obtained directly from the output of the convolutional LSTM using a non-trainable fully connected layer that automatically extracts the coordinates of the vertebra centroids from the refined probability maps generated by the convolutional LSTM. This fully connected layer between the convolutional LSTM and the shape-basis network has uniform weights and no bias term, and it generates the correct coordinates when the response (probability map) is clear. The use of this fully connected layer between the convolutional LSTM and the shape-basis network is advantageous in that is enables end-to-end training of the DI2IN, the convolutional LSTM, and the shape-basis neural network. This also enables end-to-end automated inference for a newly received 3D CT volume of a patient, in which: the DI2IN inputs the 3D volume and generates the multi-channel probability maps for the vertebra locations; the multi-channel probability maps generated by the DI2IN are directly input as a sequence (both forward and backward) to the convolutional LSTM, which generates refined probability maps for the vertebra locations; the refined probability maps generated by the convolutional LSTM are input to the fully connected layer, which automatically generates a coordinate vector of vertebra centroid locations from the refined probability maps; and the coordinate vector is input to the shape-basis neural network, which outputs a coordinate vector defining a refined coordinate vector that provides the final coordinates for the vertebra centroids in the CT volume.

Returning to step 210, the final labeled vertebra locations are output. The refined coordinate vector generated using the shape-basis network provides final coordinates in the CT volume detected/predicted for the vertebra centroid corresponding to each of the plurality of vertebra labels (e.g., C1-S2). The detected locations corresponding vertebrae labels can be output by being displayed on a display device of a computer system. For example, the detected location and possible an area surrounding the detected location for one or more of the labeled vertebrae can be highlighted in a 3D visualization of the 3D CT volume or one or more 2D slices of the 3D volume displayed on a display device of a computer system. The detected locations and corresponding labels of the vertebrae can also be stored on a memory or storage of a computer system or electronically transmitted to a remote computer system, and can be used as input to other medical image analysis algorithms, such as a segmentation algorithm.

Figure 6:
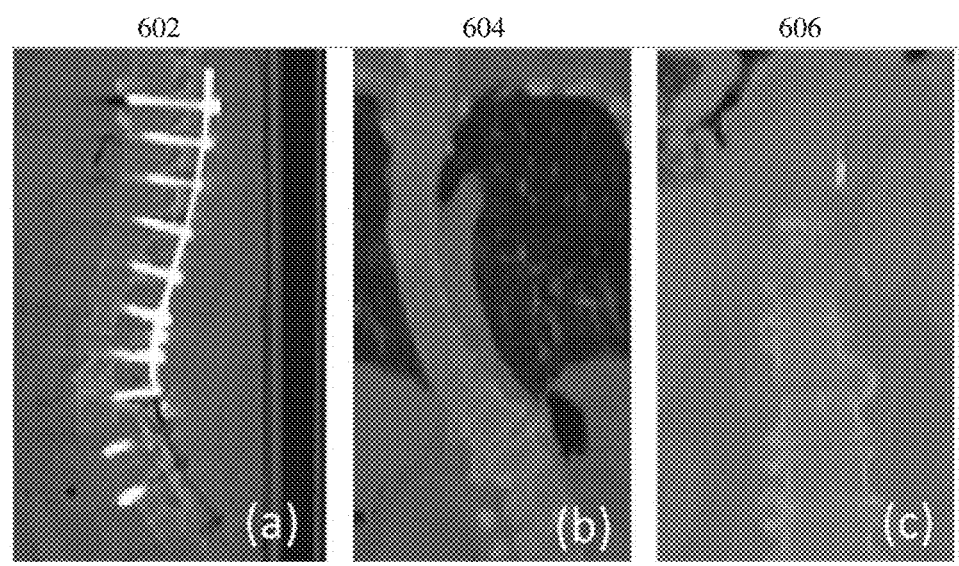
FIG. 6 illustrates examples of challenging cases for vertebrae localization and identification.

The present inventors evaluated the method described in FIGS. 1 and 2 on a database of 302 CT scans with various types of lesions. This dataset has some cases with unusual appearance, such as abnormal spinal structure and bright visual artifacts due to metal implants by post-operative procedures. Furthermore, the field-of-view (FOV) of each CT image varies greatly in terms of vertical cropping, image noise, and physical resolution. Most cases contain only part of the entire spine. The overall spinal structure can be seen in only a few examples. Large changes in lesions and limited FOV increase the complexity of the appearance of the vertebrae, making it difficult to accurately localize and identify the spinal column. FIG. 6 illustrates examples of challenging cases for vertebrae localization and identification. As shown in FIG. 6, image 602 shows a CT image with bright visual impacts due to surgical metal implants, image 604 shows a CT image with unusual spine curvature, and image 606 shows a CT image with a limited FOV. For each of the CT scans in the dataset, the ground truth was marked on the center of gravity of each vertebra and annotated by clinical experts. In Glocker et al. [1], Glocker et al. [2], Chen et al., and Suzani et al., two different settings have been conducted on this dataset: the first one uses 112 images as training and the other 112 images as testing; the second one takes all the data in the first setting plus an extra 18 images as the training data (overall 242 training images), and 60 unseen images are used as testing data. For fair comparison of the method described herein, the present inventors have followed the same configuration, which are referred to as Set 1 and Set 2, respectively, in the experiments. Table 1 compares the results of the method described herein with the numerical results reported in Glocker et al. [2], Chen et al., and Suzani et al. in terms of Euclidean distance error (mm) and identification rates (Id.Rates) defined by Glocker et al. [1]. The average mean errors of these two datasets are 10.6 mm and 8.7 mm, respectively, and the identification rates are 78% and 85% respectively. Overall, the method described herein is superior to the previous methods on the same datasets with respect to mean error and identification rate.

The present inventors collected 1000 additional CT volumes and trained the proposed end-to-end network (DI2IN-convolutional LSTM-shape-basis neural network) from scratch to verify whether training the neural network with more labeled data would improve its performance. This data set covers large visual changes of the spinal column (e.g., age, abnormality, FOV, contrast, etc.). The network trained using the 1000 CT volumes was tested on the same testing data in Set 1 and Set 2 and the results are provided in Table 1 (shown as "Our method +1000). As can be seen, adding more training data greatly improved the performance of the method, verifying that a large amount of labelled trained data will efficiently boost the power of the end-to-end network described herein. More detailed results are provided in FIG. 7.

FIG. 7 illustrates a comparison of localization errors and identification rates among different methods. As shown in FIG. 7, table 700 provides a comparison of localization errors (mm) and identification rates for Set 1 and Set 2 for all vertebrae for Glocker et al. [2], Suzani et al., Chen et al., with the method described herein ("DI2IN+ConvLSTM+ Shape"), as well as localization errors after each step ("DI2IN" and "DI2IN+ConvLSTM"). "ConvLSTM" and "Shape" denote the convolutional LSTM and the shape-basis neural network, respectively. "+1000" denotes that the network is trained with the 1000 additional CT volumes. Table 700 shows that the incorporating the convolutional LSTM and the shape-basis network with the DI2IN improves the performance of the vertebrae localization and identification. Table 700 also shows performance of the method described herein, as compared to Glocker et al. [2], Suzani et al., and Chen et al., for vertebrae in the cervical, thoracic, and lumbar regions.

Figure 8:
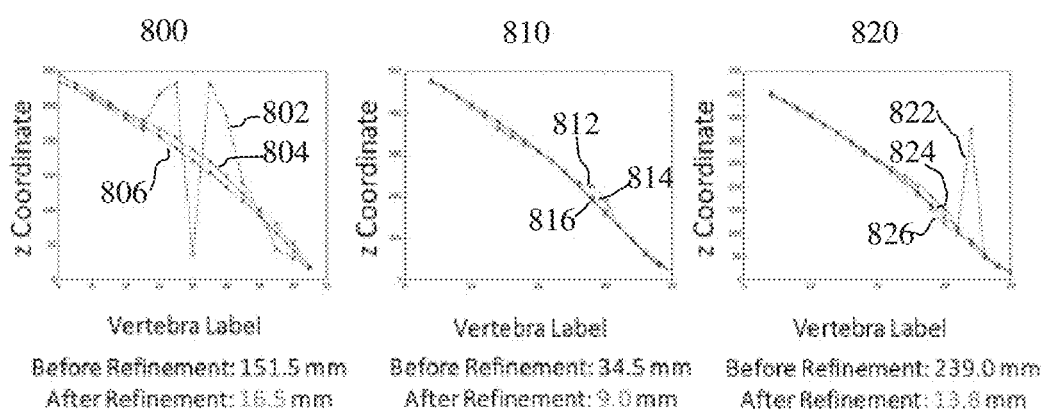
FIG. 8 illustrates an effect of refinement in the vertical direction using a shape-basis network in exemplary vertebrae localization and identification results.

FIG. 8 illustrates an effect of refinement in the vertical direction using the shape-basis network in exemplary vertebrae localization and identification results. As shown in FIG. 8, image 800 shows predicted z coordinates 802 from the Convolutional LSTM, refined z coordinates 804 output by the shape-basis network, and ground truth z coordinates 806 for vertebrae corresponding to the plurality of vertebra labels in a first CT volume. As shown in image 800, the maximum error of the vertebra localization in the vertical direction before refinement by the shape-basis network is 151.5 mm and the maximum error after refinement by the shape-basis network is 16.5 mm. Image 810 shows predicted z coordinates 812 from the Convolutional LSTM, refined z coordinates 814 output by the shape-basis network, and ground truth z coordinates 816 for vertebrae corresponding to the plurality of vertebra labels in a second CT volume. As shown in image 810, the maximum error of the vertebra localization in the vertical direction before refinement by the shape-basis network is 34.5 mm and the maximum error after refinement by the shape-basis network is 9.0 mm. Image 820 shows predicted z coordinates 822 from the Convolutional LSTM, refined z coordinates 824 output by

TABLE 1

| Region | Method | Set 1 | | | Set 2 | | |
| --- | --- | --- | --- | --- | --- | --- | --- |
| | | Mean | Std | Id. Rates | Mean | Std | Id. Rates |
| All | Glocker et al. [2] | 12.4 | 11.2 | 70% | 13.2 | 17.8 | 74% |
| | Suzani et al. | 18.2 | 11.4 | — | — | — | — |
| | Chen et al. | — | — | — | 8.8 | 13.0 | 84% |
| | Our method | 10.6 | 8.7 | 78% | 8.7 | 8.5 | 85% |
| | Our method + 1000 | 9.0 | 8.8 | 83% | 6.9 | 7.6 | 89% | the shape-basis network, and ground truth z coordinates 826 for vertebrae corresponding to the plurality of vertebra labels in a third CT volume. As shown in image 820, the maximum error of the vertebra localization in the vertical direction before refinement by the shape-basis network is 239.0 mm and the maximum error after refinement by the shape-basis network is 13.8 mm. As shown in FIG. 8, the shape-basis network takes the shape regularity of the spine into account and removes false positives, which significantly reduces the error in vertebrae localization.

Figure 9:
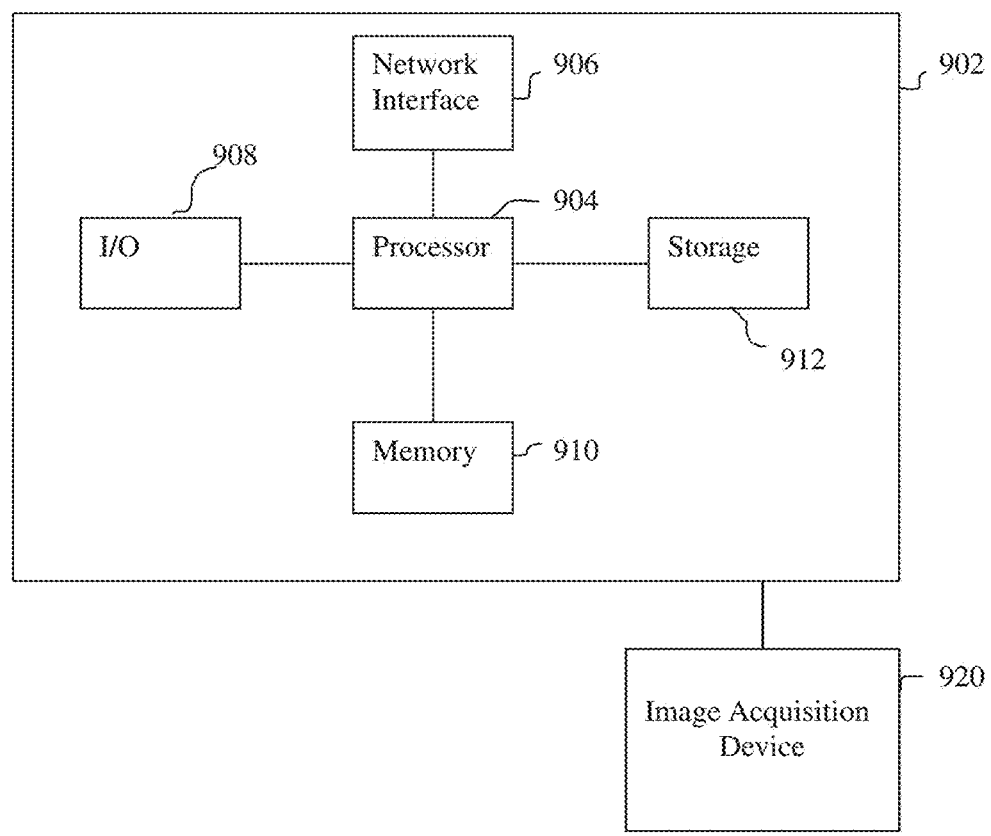
FIG. 9 is a high-level block diagram of a computer capable of implementing the present invention.

The above-described methods for automated vertebra detection and labeling may be implemented on a computer using well-known computer processors, memory units, storage devices, computer software, and other components. A high-level block diagram of such a computer is illustrated in FIG. 9. Computer 902 contains a processor 904, which controls the overall operation of the computer 902 by executing computer program instructions which define such operation. The computer program instructions may be stored in a storage device 912 (e.g., magnetic disk) and loaded into memory 910 when execution of the computer program instructions is desired. Thus, the steps of the methods of FIGS. 1 and 2 may be defined by the computer program instructions stored in the memory 910 and/or storage 912 and controlled by the processor 904 executing the computer program instructions. An image acquisition device 920, such as a CT scanner, can be connected to the computer 902 to input image data to the computer 902. It is possible to implement the image acquisition device 920 and the computer 902 as one device. It is also possible that the image acquisition device 920 and the computer 902 communicate wirelessly through a network. In a possible embodiment, the computer 902 can be located remotely with respect to the image acquisition device 920 and the method steps described herein can be performed as part of a server or cloud based service. In this case, the method steps may be performed on a single computer or distributed between multiple networked computers. The computer 902 also includes one or more network interfaces 806 for communicating with other devices via a network. The computer 902 also includes other input/output devices 908 that enable user interaction with the computer 902 (e.g., display, keyboard, mouse, speakers, buttons, etc.). Such input/output devices 908 may be used in conjunction with a set of computer programs as an annotation tool to annotate images/volumes received from the image acquisition device 920. One skilled in the art will recognize that an implementation of an actual computer could contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for automated vertebra localization and identification in a 3D computed tomography (CT) volume of a patient, comprising:

predicting initial vertebra locations in a 3D CT volume of a patient for a plurality of vertebrae corresponding to a plurality of vertebra labels using a trained deep image-to-image network (DI2IN);

refining the initial vertebra locations for the plurality of vertebrae predicted using the DI2IN using a trained recurrent neural network, resulting in an updated set of vertebra locations for the plurality of vertebrae corresponding to the plurality of vertebra labels; and determining final vertebra locations in the 3D CT volume for the plurality of vertebrae corresponding to the plurality of vertebra labels by refining the updated set of vertebra locations using a trained shape-basis deep neural network.

2. The method of claim 1, wherein predicting initial vertebra locations in a 3D CT volume of a patient for a plurality of vertebrae corresponding to a plurality of vertebra labels using a trained deep image-to-image network (DI2IN) comprises:

inputting the 3D CT volume to the trained DI2IN; and generating, by the trained DI2IN from the 3D CT volume, a plurality of probability maps, each corresponding to a respective one of the plurality of vertebra labels.

3. The method of claim 2, wherein the trained DI2IN comprises a convolutional encoder-decoder trained to perform multi-channel voxel wise regression from the 3D CT volume to generate a respective one of the plurality of probability maps on each of a plurality of channels.

4. The method of claim 3, wherein the trained DI2IN is trained based on training images and ground truth probability maps generated using a Gaussian distribution surrounding ground truth locations for the plurality vertebrae corresponding to the plurality of vertebra labels in each training image.

5. The method of claim 3, wherein the trained DI2IN is trained using a multi-level deep supervision network including a plurality of branches diverging from decoder layers of the convolutional encoder-decoder to minimize, for each of the plurality of channels, a total loss function that combines a voxel-wise loss between an output layer of each of the plurality of branches a ground truth probability map and a voxel-wise loss between a final probability map output by the decoder and the ground truth probability map over a plurality of training samples.

6. The method of claim 2, wherein the trained recurrent neural network is convolutional long short-term memory (LSTM) and refining the initial vertebra locations for the plurality of vertebrae predicted using the DI2IN using the trained recurrent neural network comprises:

sequentially inputting the plurality of probability maps generated by the DI2IN to the convolutional LSTM in an order based on respective one of the plurality of vertebra labels corresponding to each of the plurality of probability maps; and generating, by the convolutional LSTM, an updated probability map for each sequentially input probability map generated by the DI2IN.

7. The method of claim 6, wherein sequentially inputting the plurality of probability maps generated by the DI2IN to the convolutional LSTM in an order based on respective one of the plurality of vertebra labels corresponding to each of the plurality of probability maps comprises:

sequentially inputting the plurality of probability maps generated by the DI2IN to the convolutional LSTM in a forward order from a top vertebra label to a bottom vertebra label; and sequentially inputting the plurality of probability maps generated by the DI2IN to the convolutional LSTM in a backward order from the bottom vertebra label to the top vertebra label.

8. The method of claim 7, wherein generating, by the convolutional LSTM, an updated probability map for each sequentially input probability map generated by the DI2IN comprises:

generating, by the convolutional LSTM, a first updated probability map for each of plurality of probability maps generated by the DI2IN in response to sequentially inputting the plurality of probability maps in the forward order;

generating, by the convolutional LSTM, a second updated probability map for each of plurality of probability maps generated by the DI2IN in response to sequentially inputting the plurality of probability maps in the backward order; and combining the first and second updated probability maps generated for each of the plurality of probability maps.

9. The method of claim 6, wherein generating, by the convolutional LSTM, an updated probability map for each sequentially input probability map generated by the DI2IN comprises:

for each of the sequentially input probability map, generating the update probability map by the convolution LSTM based on the input probability map and a cell state and hidden state computed for a previous input one of the plurality of probability maps.

10. The method of claim 6, wherein determining final vertebra locations in the 3D CT volume for the plurality of vertebrae corresponding to the plurality of vertebra labels by refining the updated set of vertebra locations using a trained shape-basis deep neural network comprises:

determining an input coordinate vector corresponding to the updated set of vertebra locations from the updated probability maps generated by the convolutional LSTM;

inputting the input coordinate vector to the trained shape-basis deep neural network; and generating, by the trained shape-basis deep neural network, a coefficient vector that defines a refined coordinate vector corresponding to the final vertebra locations in the 3D volume as a linear combination of a shape-based dictionary learned from a set of training samples.

11. The method of claim 10, wherein determining an input coordinate vector corresponding to the update set of vertebra locations from the updated probability maps generated by the convolutional LSTM is performed by a fully connected layer between the convolutional LSTM and the trained shape-basis network, and the DI2IN, the convolutional LSTM, and the shape-basis network are trained as an end-to-end network.

12. The method of claim 1, wherein determining final vertebra locations in the 3D CT volume for the plurality of vertebrae corresponding to the plurality of vertebra labels by refining the updated set of vertebra locations using a trained shape-basis deep neural network comprises:

inputting coordinate vector corresponding to the updated set of vertebra locations to the trained shape-basis network; and generating, by the trained shape-basis deep neural network, a coefficient vector that defines a refined coordinate vector corresponding to the final vertebra locations in the 3D volume as a linear combination of a shape-based dictionary learned from a set of training samples.

13. An apparatus for automated vertebra localization and identification in a 3D computed tomography (CT) volume of a patient, comprising:

means for predicting initial vertebra locations in a 3D CT volume of a patient for a plurality of vertebrae corresponding to a plurality of vertebra labels using a trained deep image-to-image network (DI2IN);

means for refining the initial vertebra locations for the plurality of vertebrae predicted using the DI2IN using a trained recurrent neural network, resulting in an updated set of vertebra locations for the plurality of vertebrae corresponding to the plurality of vertebrae labels; and means for determining final vertebra locations in the 3D CT volume for the plurality of vertebrae corresponding to the plurality of vertebra labels by refining the updated set of vertebra locations using a trained shape-basis deep neural network.

14. The apparatus of claim 13, wherein the means for predicting initial vertebra locations in a 3D CT volume of a patient for a plurality of vertebrae corresponding to a plurality of vertebra labels using a trained deep image-to-image network (DI2IN) comprises:

means for generating, by the trained DI2IN from the 3D CT volume, a plurality of probability maps, each corresponding to a respective one of the plurality of vertebra labels.

15. The apparatus of claim 14, wherein the trained recurrent neural network is convolutional long short-term memory (LSTM) and the means for refining the initial vertebra locations for the plurality of vertebrae predicted using the DI2IN using the trained recurrent neural network comprises:

means for sequentially inputting the plurality of probability maps generated by the DI2IN to the convolutional LSTM in an order based on respective one of the plurality of vertebra labels corresponding to each of the plurality of probability maps; and means for generating, by the convolutional LSTM, an updated probability map for each sequentially input probability map generated by the DI2IN.

16. The apparatus of claim 13, wherein the means for determining final vertebra locations in the 3D CT volume for the plurality of vertebrae corresponding to the plurality of vertebra labels by refining the updated set of vertebra locations using a trained shape-basis deep neural network comprises:

means for generating, by the trained shape-basis deep neural network based on an input coordinate vector corresponding to the updated set of vertebra locations, a coefficient vector that defines a refined coordinate vector corresponding to the final vertebra locations in the 3D volume as a linear combination of a shape-based dictionary learned from a set of training samples.

17. A non-transitory computer readable medium storing computer program instructions for automated vertebra localization and identification in a 3D computed tomography (CT) volume of a patient, the computer program instructions when executed by a processor cause the processor to perform operation comprising:

predicting initial vertebra locations in a 3D CT volume of a patient for a plurality of vertebrae corresponding to a plurality of vertebra labels using a trained deep image-to-image network (DI2IN);

refining the initial vertebra locations for the plurality of vertebrae predicted using the DI2IN using a trained recurrent neural network, resulting in an updated set of vertebra locations for the plurality of vertebrae corresponding to the plurality of vertebrae labels; and determining final vertebra locations in the 3D CT volume for the plurality of vertebrae corresponding to the plurality of vertebra labels by refining the updated set of vertebra locations using a trained shape-basis deep neural network.

18. The non-transitory computer readable medium of claim 17, wherein predicting initial vertebra locations in a 3D CT volume of a patient for a plurality of vertebrae corresponding to a plurality of vertebra labels using a trained deep image-to-image network (DI2IN) comprises:

inputting the 3D CT volume to the trained DI2IN; and
generating, by the trained DI2IN from the 3D CT volume, a plurality of probability maps, each corresponding to a respective one of the plurality of vertebra labels.

19. The non-transitory computer readable medium of claim 18, wherein the trained DI2IN comprises a convolutional encoder-decoder trained to perform multi-channel voxel wise regression from the 3D CT volume to generate a respective one of the plurality of probability maps on each of a plurality of channels.

20. The non-transitory computer readable medium of claim 18, wherein the trained recurrent neural network is convolutional long short-term memory (LSTM) and refining the initial vertebra locations for the plurality of vertebrae predicted using the DI2IN using the trained recurrent neural network comprises:

sequentially inputting the plurality of probability maps generated by the DI2IN to the convolutional LSTM in an order based on respective one of the plurality of vertebra labels corresponding to each of the plurality of probability maps; and
generating, by the convolutional LSTM, an updated probability map for each sequentially input probability map generated by the DI2IN.

21. The non-transitory computer readable medium of claim 20, wherein sequentially inputting the plurality of probability maps generated by the DI2IN to the convolutional LSTM in an order based on respective one of the plurality of vertebra labels corresponding to each of the plurality of probability maps comprises:

sequentially inputting the plurality of probability maps generated by the DI2IN to the convolutional LSTM in a forward order from a top vertebra label to a bottom vertebra label, and sequentially inputting the plurality of probability maps generated by the DI2IN to the convolutional LSTM in a backward order from the bottom vertebra label to the top vertebra label; and wherein generating, by the convolutional LSTM, an updated probability map for each sequentially input probability map generated by the DI2IN comprises:

generating, by the convolutional LSTM, a first updated probability map for each of plurality of probability maps generated by the DI2IN in response to sequentially inputting the plurality of probability maps in the forward order, generating, by the convolutional LSTM, a second updated probability map for each of plurality of probability maps generated by the DI2IN in response to sequentially inputting the plurality of probability maps in the backward order, and combining the first and second updated probability maps generated for each of the plurality of probability maps.

22. The non-transitory computer readable medium of claim 20, wherein determining final vertebra locations in the 3D CT volume for the plurality of vertebrae corresponding to the plurality of vertebra labels by refining the updated set of vertebra locations using a trained shape-basis deep neural network comprises:

determining an input coordinate vector corresponding to the updated set of vertebra locations from the updated probability maps generated by the convolutional LSTM;

inputting the input coordinate vector to the trained shape-basis deep neural network; and generating, by the trained shape-basis deep neural network, a coefficient vector that defines a refined coordinate vector corresponding to the final vertebra locations in the 3D volume as a linear combination of a shape-based dictionary learned from a set of training samples.

23. The non-transitory computer readable medium of claim 22, wherein determining an input coordinate vector corresponding to the update set of vertebra locations from the updated probability maps generated by the convolutional LSTM is performed by a fully connected layer between the convolutional LSTM and the trained shape-basis network, and the DI2IN, the convolutional LSTM, and the shape-basis network are trained as an end-to-end network.

* * * * *